United States Patent
Deuerlein et al.

(10) Patent No.: US 8,568,677 B2
(45) Date of Patent: Oct. 29, 2013

(54) P/S-TM-COMPRISING ZEOLITES FOR DECOMPOSITION OF $N_2O$

(75) Inventors: Stephan Deuerlein, Ludwigshafen (DE); Tobias Rosendahl, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/271,550

(22) Filed: Oct. 12, 2011

(65) Prior Publication Data

US 2012/0087851 A1    Apr. 12, 2012

Related U.S. Application Data

(60) Provisional application No. 61/392,049, filed on Oct. 12, 2010.

(51) Int. Cl.
*B01D 53/56* (2006.01)
*B01J 29/00* (2006.01)

(52) U.S. Cl.
USPC .......... 423/239.1; 423/213.2; 423/390.1; 423/393; 562/590; 502/60

(58) Field of Classification Search
USPC ......... 423/239.2, 213.2, 390.1, 393; 562/590; 502/60
See application file for complete search history.

(56) References Cited

U.S. PATENT DOCUMENTS

| 4,359,406 A * | 11/1982 | Fung ............................ 502/200 |
| 5,422,333 A * | 6/1995 | Kano et al. .................... 502/60 |
| 5,427,753 A * | 6/1995 | Miura et al. ................. 423/239.2 |
| 7,141,526 B2 * | 11/2006 | Yoshikawa ...................... 502/74 |
| 7,695,703 B2 * | 4/2010 | Sobolevskiy et al. ....... 423/239.2 |
| 7,767,175 B2 * | 8/2010 | Golden et al. .............. 423/213.2 |
| 2004/0110627 A1 | 6/2004 | Schwefer et al. |
| 2004/0121899 A1 * | 6/2004 | Balmer-Millar et al. ....... 502/60 |
| 2005/0244320 A1 | 11/2005 | Schwefer et al. |
| 2008/0241034 A1 | 10/2008 | Schwefer et al. |
| 2010/0034717 A1 | 2/2010 | Adelmann et al. |
| 2011/0250127 A1 | 10/2011 | Fedeyko et al. |

FOREIGN PATENT DOCUMENTS

| CN | 101528326 A | 9/2009 |
| CN | 101730575 A | 6/2010 |
| DE | 101 12 396 A1 | 10/2002 |
| DE | 102 15 605 A1 | 10/2003 |
| DE | 10 2005 022 650 A1 | 11/2006 |
| KR | 2009-0040080 A | 4/2009 |
| WO | WO-03/084646 A1 | 10/2003 |

OTHER PUBLICATIONS

International Search Report and Written Opinion for PCT/IB2011/054458, mailed Feb. 9, 2012.

* cited by examiner

*Primary Examiner* — Timothy Vanoy
(74) *Attorney, Agent, or Firm* — Novak Druce Connolly Bove + LLP

(57) ABSTRACT

The present invention relates to the use of a zeolite catalyst comprising at least one transition metal and in addition sulfur and/or phosphorus atoms for reducing the content of nitrogen oxides in a gas, and also to a process for reducing the content of nitrogen oxides in a gas by bringing this gas into contact with such a zeolite catalyst.

17 Claims, No Drawings

P/S-TM-COMPRISING ZEOLITES FOR DECOMPOSITION OF N₂O

CROSS-REFERENCE TO RELATED APPLICATIONS

This application claims benefit under 35 U.S.C. §119(e) of U.S. Provisional Patent App. Ser. No. 61/392,049, filed Oct. 12, 2010, which is incorporated herein by reference in its entirety.

The present invention relates to the use of a zeolite catalyst comprising at least one transition metal and in addition sulfur and/or phosphorus atoms for reducing the content of nitrogen oxides in a gas, and also to a process for reducing the content of nitrogen oxides in a gas by bringing this gas into contact with such a zeolite catalyst.

The use of metal-doped catalysts in processes for the catalytic removal of nitrogen oxides is known from the prior art.

DE 101 12 396 A1 discloses a process for reducing the content of $N_2O$ in gases. Here, a selected zeolite catalyst is used. This is present in the H form and/or comprises exchanged iron and is characterized by the presence of non-lattice aluminum in addition to the lattice aluminum in a molar ratio of from 1:2 to 20:1. Furthermore, this document discloses that dealumination or demetallation can be carried out by means of a mineral acid treatment. This is carried out using acids selected from among HCl, HF, $H_2SO_4$, $HNO_3$ and $H_3PO_4$. The acid treatment as described in DE 101 12 396 A1 is not carried out to introduce sulfur and/or phosphorus atoms onto the catalyst. No content of sulfur and/or phosphorus atoms in the finished catalyst is disclosed in this document.

WO 03/084646 A1 discloses a process for reducing the content of $NO_x$ and $N_2O$ in gases, in particular in process gases and offgases, which comprises addition of at least one nitrogen-comprising reducing agent to the $NO_x$- and $N_2O$-comprising gas in an amount not less than that required for complete reduction of the $NO_x$, addition of a hydrocarbon, carbon monoxide, hydrogen or a mixture of one or more of these gases to the $NO_x$- and $N_2O$-comprising gas to reduce the $N_2O$ and introduction of the gas mixture into at least one reaction zone which has temperatures of up to 450° C. and comprises one or more iron-laden zeolites. According to this process, catalysts which are based on zeolites into which iron has been introduced by means of solid-state ion exchange are used. For this purpose, commercially available ammonium zeolites are usually treated with appropriate iron salts, e.g. $FeSO_4.7 H_2O$. After calcination, the iron-comprising zeolites are thoroughly washed in distilled water, filtered off and dried. Thus, the document cited discloses zeolite catalysts which are doped with iron. However, the sulfate anions which are likewise applied together with the iron cations are removed again by means of the thorough washing, so that no sulfur is present on the iron-doped catalyst.

DE 102 15 605 A1 likewise discloses a process for reducing the content of $NO_x$ and $N_2O$ in gases, in particular in process gases and offgases, where the gas to be treated is brought into contact with a catalyst which is based on a zeolite and is doped with iron. According to this document, the doping with iron can likewise be achieved by applying $FeSO_4.7 H_2O$ to the zeolite. Moreover, here too, the sulfate anions are removed again by thorough washing, so that no sulfur and/or phosphorus atoms are present In the final catalyst.

DE 10 2005 022 650 A1 also discloses a process for reducing the content of nitrogen oxides in gases. For this purpose, the gas to be treated is brought into contact with a zeolite which is doped with copper and/or iron atoms. The presence of sulfur or phosphorus atoms on the zeolite catalyst is likewise not disclosed in this document.

The catalysts known from the prior art, in particular the iron-doped zeolites, have an activity for the degradation of nitrogen oxides in gases which is still capable of improvement. Furthermore, there is a need for an improved zeolite catalyst which has the same activity as the systems known from the prior art even at low temperatures, or displays a correspondingly higher activity at the same temperature. A catalyst which displays a sufficiently high activity even at a relatively low reaction temperature would be advantageous because the offgas from many industrial plants has a low temperature and heating of this offgas before reaction over the appropriate catalyst is unattractive for ecological and economic reasons.

The objects mentioned in the light of the available prior art are achieved, according to the invention, by the use of a zeolite catalyst for reducing the content of nitrogen oxides in a gas, where the zeolite catalyst comprises at least one transition metal and in addition sulfur and/or phosphorus atoms.

The objects are also achieved by a process for reducing the content of nitrogen oxides in a gas by bringing the gas into contact with a zeolite catalyst as defined above.

The zeolite catalyst used according to the invention will be described in detail below:

The basis of the zeolite catalyst used according to the invention is a zeolite. Zeolites are known per se to those skilled in the art and are disclosed, for example, in *Catalysis and Zeolites, Fundamentals and Applications*, J. Weitkamp, I. Puppe, (eds), Springer-Verlag, Berlin, Heidelberg 1990.

In general, all zeolites known to those skilled in the art are suitable for the zeolite catalyst used according to the invention. These are named in the following using the three letter nomenclature of the IZA (international zeolite association) structure commission known to those skilled in the art.

Zeolites which are particularly suitable for the purposes of the invention are selected from the group consisting of BEA, CHA, FAU, FER and MFI and mixtures thereof.

According to the invention, the zeolite catalyst comprises at least one transition metal. The term transition metal is known per se to those skilled in the art and describes the group of elements in transition groups 3 to 12 of the Periodic Table of the Elements (new IUPAC nomenclature).

In a preferred embodiment, the catalyst used according to the invention comprises at least one transition metal selected from the fourth period and/or groups 8 to 11 of the Periodic Table of the Elements.

The present invention therefore relates particularly to the use according to the invention where the at least one transition metal is selected from the fourth period and/or groups 8 to 11 of the Periodic Table of the Elements.

The catalyst used according to the invention more preferably comprises at least one transition metal selected from the group consisting of Sc, Ti, V, Cr, Mn, Fe, Co, Ni, Cu, Zn, Ru, Rh, Pd, Ag, Os, Ir, Pt, Au and mixtures thereof.

The present invention therefore relates particularly to the use according to the invention where the at least one transition metal is selected from the group consisting of Sc, Ti, V, Cr, Mn, Fe, Co, Ni, Cu, Zn, Ru, Rh, Pd, Ag, Os, Ir, Pt, Au and mixtures thereof.

In a particularly preferred embodiment, the catalyst used according to the invention comprises Fe, Cu, Co and/or Ni, very particularly preferably Fe, as at least one transition metal.

The present invention therefore very particularly preferably relates to the use according to the invention where the at least one transition metal is Fe, Cu, Co and/or Ni.

Examples according to the invention of nitrogen oxides are preferably selected from the group consisting of dinitrogen monoxide $N_2O$, nitrogen oxides $NO_x$, where x is 1 or 2, and mixtures thereof. In a preferred embodiment, the gas to be treated comprises a little ($NO_x/N_2O<0.5$) and in particular no nitrogen oxides $NO_x$. In a preferred embodiment, a stage for decreasing the amount of $NO_x$ therefore precedes the use according to the invention. Methods of decreasing the amount of $NO_x$ are known to those skilled in the art.

The content of the nitrogen oxide $N_2O$ is particularly preferably reduced by means of the use according to the invention.

The at least one transition metal which is present according to the invention can generally be comprised in the zeolite catalyst used according to the invention in any amount which gives the catalyst used according to the invention a particularly high activity, for example in the degradation of nitrogen oxides, in particular dinitrogen monoxide $N_2O$.

In a preferred embodiment, the at least one transition metal is present in the catalyst used according to the invention in a concentration of from 0.1 to 10.0% by weight, particularly preferably from 0.25 to 5.0% by weight, very particularly preferably from 0.5 to 2.5% by weight, for example 0.7 or 2.5% by weight, in each case based on the total zeolite catalyst.

In a preferred embodiment, the present invention therefore relates to the use according to the invention where the at least one transition metal is present in a concentration of from 0.1 to 10.0% by weight, particularly preferably from 0.25 to 5.0% by weight, very particularly preferably from 0.5 to 2.5% by weight, for example 0.7 or 2.5% by weight, in each case based on the total zeolite catalyst.

The at least one transition metal which is present according to the invention can be present in either cationic or elemental form in the zeolite catalyst used according to the invention. If the transition metal is present in cationic form, it is preferably present in oxidation numbers which are typical of the respective transition metal as a result of its position in the Periodic Table. In the preferred case of iron being present as transition metal in the zeolite catalyst used according to the invention, the oxidation number thereof is preferably +2 or +3. If the at least one transition metal is present in elemental form, it has the oxidation number 0. The at least one transition metal can also be present as a mixture of various oxidation numbers.

It is possible, according to the invention, for the at least one transition metal present to be incorporated into the lattice of the respective zeolite and/or to be present outside this lattice structure as nonlattice transition metal.

Furthermore, the zeolite catalyst used according to the invention additionally comprises sulfur and/or phosphorus atoms.

In the zeolite catalyst used according to the invention, the sulfur and/or phosphorus atoms can generally be present in any amount which, in combination with the at least one transition metal present, gives the zeolite catalyst used according to the invention a particularly high activity in the degradation of nitrogen oxides, in particular dinitrogen monoxide $N_2O$.

In a preferred embodiment, sulfur and/or phosphorus atoms are present in the catalyst used according to the invention in a concentration of less than 10% by weight, based on the total catalyst.

In a further preferred embodiment, sulfur and/or phosphorus atoms are present in the catalyst according to the invention in a concentration of less than 3% by weight, very particularly preferably from 0.2 to 2.5% by weight, in each case based on the total catalyst.

The present invention therefore also preferably provides for the use according to the invention in which the sulfur and/or phosphorus atoms are present in a concentration of less than 10% by weight, preferably less than 3% by weight, particularly preferably from 0.2 to 2.0% by weight, based on the total catalyst.

The sulfur and/or phosphorus atoms which are present according to the invention can be present in a uniform oxidation state or in combinations of various oxidation states in the zeolite catalyst used according to the invention. In the embodiment of the invention in which sulfur is present in the zeolite catalyst according to the invention, this sulfur is preferably present in the oxidation state +6 or +2 or a combination of these side by side, but in particular the oxidation state +6.

In the embodiment of the invention in which phosphorus is present in the zeolite catalyst according to the invention, this phosphorus is preferably present in the oxidation state +5 or +3 or a combination of these side by side, but in particular the oxidation state +5.

Sulfur and/or phosphorus can be incorporated into the lattice of the respective zeolite, or sulfur and/or phosphorus are present as atoms, cations or anions outside the lattice of the zeolite, or sulfur and/or phosphorus are present both in the lattice and also outside the lattice of the respective zeolite.

The zeolite catalysts used according to the invention generally comprise aluminum in cationic form which is present in the lattice. The zeolite catalyst used according to the invention can, in a further embodiment, comprise not only the aluminum cations present in the lattice but also corresponding cations which are present outside the lattice as nonlattice aluminum cations.

Steaming of the zeolites, i.e. hydrothermal treatment of the zeolites by passing steam over them at elevated temperatures, or else treatment with acids are particularly useful for setting a preferred ratio of nonlattice aluminum to lattice aluminum. A combination of various methods can also be employed.

In a treatment with $H_2O$ vapor and/or acid, as is known to those skilled in the art, dealumination or, if the zeolite comprises other metals such as Fe, Ga, etc., in addition to Al, demetallation, i.e. removal of the aluminum or these metals from the lattice of the zeolite, takes place. The aluminum or the metals migrate from their lattice positions into the pores of the zeolite and remain there as amorphous constituents in oxidic or hydroxidic form as extralattice metal. The degree of dealumination or demetallation can be set via the duration of the treatment and the reagent concentration. Part of the extralattice metal produced can also be removed from the pores during the treatment. As a result, the metal content of the catalyst can change.

The treatment of the zeolite with steam can, for example, be carried out at temperatures of from 300 to 800° C. for a period of from 0.5 to 48 hours. The zeolite can be exposed to pure steam or a mixture of nitrogen and/or air and water vapor having a proportion of water vapor of from 1 to 100% by weight at total pressures of up to 100 bar. A carrier gas can optionally be added to the steam or the water vapor mixture. Suitable carrier gases are inert under the treatment conditions; examples are $N_2$, Ar, He, $H_2$ or a mixture thereof.

The zeolites can be dealuminated/demetallated further by means of an additional mineral acid treatment, optionally in addition to the steam treatment. The acid treatment can both remove extralattice metal from the pores and lead to further demetallation of the lattice. This step can, for example, be carried out in a batch reactor at temperatures of from 0 to 120° C. at a lattice/zeolite ratio of from 1 to 100 cm³/g and acid concentrations of from 0.001 M to the maximum concentration of the acid. Examples of acids which can be used for this step are HCl, HF, $H_2SO_4$, $HNO_3$ and $H_3PO_4$. After the acid treatment, the zeolite is separated off from the reaction mixture by conventional methods, e.g. by filtration or centrifugation.

According to the present invention, amorphous metal oxides or hydroxides are produced at extralattice sites by the above-described treatment of the zeolite and it is assumed that they act as catalytic sites to increase the activity in respect of the degradation of $N_2O$.

The zeolite catalyst used according to the invention can comprise, in addition to the above-described zeolite, the at least one transition metal and sulfur and/or phosphorus atoms, further customary components known to those skilled in the art, for example binders such as aluminum oxide or silicon oxide and mixtures thereof.

The zeolite catalyst used according to the invention can be used in any form which appears to be suitable to a person skilled in the art, for example as shaped bodies, e.g. extrudates or honeycomb bodies, crushed material, particles or powder. In industry, the zeolite catalyst used according to the invention is preferably used in the form of shaped bodies, for example having a particle diameter of from 1 to 10 mm, preferably from 1.5 to 5 mm.

The catalyst used according to the invention can, for example, be produced by a process which comprises the following steps:
(A) application of the at least one transition metal or a precursor compound thereof to a zeolite,
(B) calcination of the zeolite from step (A) to convert, if applicable, the precursor compound into the at least one transition metal and to obtain a zeolite comprising the at least one transition metal,
(C) application of the sulfur and/or phosphorus atoms or a precursor compound thereof to the doped zeolite from step (B) and
(D) calcination of the zeolite from step (C) to obtain the catalyst to be used according to the invention.

The individual steps of the process for producing the catalyst used according to the invention are described in detail below:

Step (A):

Step (A) comprises application of the at least one transition metal or a precursor compound thereof to a zeolite.

According to the invention, it is generally possible to use all zeolites which have been mentioned above. In a preferred embodiment, zeolites selected from the group consisting of BEA, FAU, FER, MFI and mixtures thereof are used.

In a preferred embodiment, precursor compounds of the abovementioned transition metals, particularly preferably the metals Fe, Cu, Co, Ni or mixtures thereof, are used for this purpose.

Particularly preferred precursor compounds for the transition metal iron which is very particularly preferably used are $Fe(NO_3)_2$ and $Fe(SO_4)$.

Step (A) of the process is particularly preferably carried out by dissolving a suitable amount of the appropriate precursor compounds in water or an aqueous solution and impregnating the appropriate zeolites with this aqueous solution. The aqueous solutions which are preferably used can, in one embodiment, comprise water as solvent. In a further embodiment, the aqueous solutions can comprise not only water but also further, polar and water-miscible solvents, for example alcohols such as methanol, ethanol, propanols and mixtures thereof.

Impregnation of a solid with an aqueous solution is known per se to those skilled in the art. Impregnation is preferably carried out by spraying the impregnation solution of the appropriate transition metal or a precursor compound thereof onto the zeolite.

The amount of aqueous impregnation solution or the amount of transition metal or precursor compound of the at least one transition metal present in this impregnation solution is set so that an appropriate amount of transition metal is present on the zeolite after application to the zeolite and drying and calcination. Methods of determining the appropriate amounts are known to those skilled in the art.

In one embodiment of the process, the water present on the zeolite after application of the at least one metal according to step (A) of the process is removed, for example by drying. Methods of drying a solid are known per se to those skilled in the art, for example filtration, centrifugation and/or heating. In a preferred embodiment, drying of the zeolite after process step (A) is effected by heat treatment at a temperature in the range from, for example, 10 to 150° C. and a pressure of, for example, atmospheric pressure or a reduced pressure of, for example, less than 800 mbar. The transition metal-comprising zeolite which has preferably been dried in this way is preferably transferred directly to step (B).

Step (B):

Step (B) comprises calcination of the zeolite from step (A) to convert, if applicable, the precursor compound into the at least one transition metal and to obtain a zeolite comprising the at least one transition metal.

Calcination of a solid is known per se to those skilled in the art. The zeolite which has been doped with metal cations in step (A) is preferably calcined at a calcination temperature of from 300 to 700° C., preferably from 400 to 600° C., particularly preferably from 450 to 580° C. Calcination can generally be carried out in any suitable atmosphere. Preference is given to using an inert atmosphere, for example a nitrogen atmosphere.

Calcination is carried out until an appropriately doped zeolite catalyst is obtained. For example, calcination is carried out for from 1 to 10 hours, preferably from 3 to 6 hours.

In step (B) of the process, any water still present from the impregnation step (A) and/or any water of crystallization present and/or any organic solvent present is/are firstly removed. In addition, the precursor compound of the at least one transition metal which is preferably used is converted into the corresponding transition metal and/or transition metal oxide and/or the at least one transition metal is at least partly incorporated into the lattice structure of the zeolite.

Step (C):

Step (C) comprises application of the sulfur and/or phosphorus atoms or a precursor compound thereof to the doped zeolite from step (B).

Preference is given to applying at least one precursor compound of the sulfur and/or phosphorus atoms in step (C) of the process. Examples of appropriate precursor compounds are selected from the group consisting of sulfurous acid $H_2SO_3$, sulfuric acid $H_2SO_4$, phosphinic acid $H_3PO_2$, phosphonic acid $H_3PO_3$, phosphoric acid $H_3PO_4$ and mixtures thereof. Preference is given to sulfuric acid and/or phosphoric acid.

In a preferred embodiment, the doped zeolite obtained in step (B) is impregnated with an aqueous solution of the appropriate precursor compound. As indicated for step (A), an aqueous solution comprising water can be used. It is also possible to use an aqueous solution comprising, in addition to water, a polar, water-soluble solvent, for example alcohols such as methanol, ethanol, propanols or mixtures thereof, in step (C). An aqueous solution comprising water as solvent is preferably used in step (C). Very particular preference is given to using an aqueous solution of phosphoric acid or an aqueous solution of sulfuric acid or a mixture of these two aqueous solutions in step (C).

Impregnation can be carried out by methods known per se to those skilled in the art, for example by bringing the zeolite from step (B) into contact with the abovementioned aqueous solutions in a stirred reactor or by spraying the solutions onto the zeolite.

After impregnation, the impregnated zeolite can be dried by all methods known to those skilled in the art. Appropriate methods have been mentioned for step (A) and apply analogously to step (C).

In the process, it is preferred that no washing of the zeolite catalyst takes place during or after step (C) since otherwise sulfur and/or phosphorus atoms would be removed again, which is undesirable for the purposes of the invention.

Step (D):

Step (D) of the process comprises (D) calcination of the zeolite from step (C) in order to obtain the catalyst used according to the invention.

Calcination of a solid is known per se to those skilled in the art. The zeolite which has been doped with transition metal cations and sulfur and/or phosphorus atoms in step (D) is preferably calcined at a calcination temperature of from 300 to 700° C., preferably from 400 to 600° C., particularly preferably from 450 to 580° C. Calcination can generally be carried out in any suitable atmosphere. Preference is given to using an inert atmosphere, for example a nitrogen atmosphere.

Calcination is carried out until an appropriately doped zeolite catalyst is obtained. For example, calcination is carried out for from 1 to 10 hours, preferably from 3 to 6 hours.

In step (D) of the process, any water still present from the impregnation step (C) and/or any organic solvent present is/are firstly removed. In addition, the precursor compound of the sulfur and/or phosphorus atoms which is preferably used is converted into the sulfur and/or phosphorus atoms or oxides thereof and/or the sulfur and/or phosphorus atoms are at least partly incorporated into the lattice structure of the zeolite and/or form a compound with the at least one transition metal from step (A).

The steps (A) and (C) can optionally also be combined. This can be effected, for example, by the above-described transition metal solution and the above-described solution comprising sulfur and/or phosphorus atoms being applied in succession or simultaneously without intermediate calcination and intermediate drying. As an alternative, steps (A) and (C) can also be carried out directly in succession without the intermediate step (B).

An optional dealumination or demetallation of the zeolite catalyst to be used according to the invention can be carried out at any point in the production process mentioned by way of example, in particular before step (A) and/or before step (C) and/or after step (D). The dealumination or demetallation of a zeolite is known in principle to those skilled in the art.

For example, dealumination or demetallation can be effected by treatment with $H_2O$ vapor. The degree of dealumination or demetallation can be set via the duration of the steam treatment. The treatment of the zeolite with steam can, for example, be carried out at temperatures of from 300 to 800° C. for a period of from 0.5 to 48 hours. The zeolite can be exposed to pure steam or a mixture of nitrogen and/or air and steam having a proportion of water vapor of from 1 to 100% by weight at total pressures up to 100 bar. A carrier gas can optionally be added to the steam or the water vapor mixture. Suitable carrier gases are inert under the treatment conditions; examples are $N_2$, Ar, He, $H_2$ or a mixture thereof.

The zeolites can, optionally in addition to the steam treatment, also be dealuminated/demetallated by means of a mineral acid treatment. The acid treatment can both remove extralattice metal from the pores and lead to a further demetallation of the lattice. This step can, for example, be carried out in a batch reactor at temperatures of from 0 to 120° C. at an acid/zeolite ratio of from 1 to 100 $cm^3/g$ and at acid concentrations of from 0.001 M to the maximum concentration of the acid. Examples of acids which can be used for this step are HCl, HF, $H_2SO_4$, $HNO_3$ and $H_3PO_4$. After the acid treatment, the zeolite is separated from the reaction mixture by conventional methods, e.g. by filtration or centrifugation.

After production of the zeolite catalyst to be used according to the invention is complete, this catalyst can be converted into a suitable form. This is generally carried out by processes known to those skilled in the art, for example pressing, pelletization, sieving, crushing, extrusion. Industrially, the zeolite catalyst used according to the invention is preferably used in the form of shaped bodies, e.g. extrudates or honeycomb bodies, for example having a particle diameter of from 1 to 10 mm, preferably from 1.5 to 5 mm. As an alternative, the zeolite can be used as starting material in a suitable form in the production of the catalyst used according to the invention.

The use according to the invention can generally be employed in all applications in which the content of nitrogen oxides in a gas is to be reduced. In a preferred embodiment, the invention is used in nitric acid production, in adipic acid production, for power station offgases, for gas turbines or for automobile catalysts in the low-temperature range. Process gases and offgases comprising nitrogen oxide are obtained in these processes and the nitrogen oxides can be removed inexpensively by means of the process described here.

The present invention therefore preferably relates to the use according to the invention in nitric acid production, in adipic acid production, for power station offgases, for gas turbines or for automobile catalysts in the low-temperature range, particularly preferably in nitric acid production.

The present invention also provides a process for reducing the content of nitrogen oxides in a gas by bringing the gas into contact with a zeolite catalyst as defined above.

In a preferred embodiment, gases to be treated according to the invention comprise nitrogen oxides selected from the group consisting of dinitrogen monoxide $N_2O$, nitrogen oxides $NO_x$, where x is 1 or 2, and mixtures thereof. In a preferred embodiment, the gas to be treated contains little ($NO_x/N_2O<0.5$) and in particular no nitrogen oxides $NO_x$. Therefore, a stage for removal of $NO_x$ is inserted upstream in a preferred embodiment of the process of the invention. Processes for removal of $NO_x$ are known to those skilled in the art.

Particular preference is given to the nitrogen oxide $N_2O$ being catalytically degraded by means of the process of the invention so that there is overall a reduction in the content of this gas in the gas to be treated.

The gas to be treated according to the invention has a content of dinitrogen monoxide $N_2O$ of, for example, from 10 ppm by volume to 20% by volume, preferably from 200 ppm by volume to 10% by volume, particularly preferably from 500 to 2000 ppm by volume.

There is no restriction with regard to the further components present in the gas to be treated. Routine and therefore preferred further components comprised in the gas to be treated according to the invention are selected from the group consisting of water, oxygen, NO, $NO_2$, $NH_3$ and $N_2$ and mixtures thereof.

In general, the temperature at which the gas to be treated is brought into contact with the zeolite catalyst in the reaction zone is less than 500° C., preferably less than 400° C., very particularly preferably from 250 to 400° C.

The present invention therefore preferably provides the process of the invention carried out at a temperature of less than 400° C., very particularly preferably from 250 to 400° C.

In a further embodiment, various zeolite catalysts to be used according to the invention or one or more zeolite catalysts to be used according to the invention in combination with further catalysts known to those skilled in the art can be used. When a plurality of different zeolite catalysts and optionally other catalysts are used, these can be mixed with one another or be arranged in succession in the reactor. The latter arrangement is particularly advantageous when the zeolite catalyst arranged at the inlet end catalyzes particularly $NO_x$ decomposition, optionally in the presence of nitrogen-comprising reducing agents, and/or the zeolite catalyst arranged at the outlet end catalyzes particularly the decomposition of $N_2O$.

Particular preference is given to using a uniform above-described zeolite catalyst in the process of the invention.

The reaction zone can, for the purposes of the present invention, in principle be configured in any desired way. It can be present, for example, in a tube reactor or radial basket reactor.

The gas laden with nitrogen oxides is usually passed over the catalyst at a space velocity of from 200 to 200 000 $h^{-1}$, preferably from 5000 to 50 000 $h^{-1}$, particularly preferably from 10 000 to 30 000 $h^{-1}$, based on the catalyst volume. For the present purposes, the term space velocity refers to the ratio of the volume of gas mixture under STP per hour to the volume of catalyst. The space velocity can thus be adjusted via the flow velocity of the gas and/or via the amount of catalyst.

The process of the invention is preferably carried out at a GHSV (gas hourly space velocity) of from 2000 to 200 000 standard $l_{gas}/l_{cat}h$ (standard l: standard liters-gas volume at STP), particularly preferably from 5000 to 50 000 standard $l_{gas}/l_{cat}h$ very particularly preferably from 10 000 to 30 000 standard $l_{gas}/l_{cat}h$.

The present invention therefore provides, in particular, the process of the invention in which the GHSV (gas hourly space velocity) is from 2000 to 200 000 standard $l_{gas}/l_{cat}h$ (standard l: standard liters-gas volume at SIP), particularly preferably from 5000 to 50 000 standard $l_{gas}/l_{cat}h$, very particularly preferably from 10 000 to 30 000 standard $l_{gas}/l_{cat}h$.

The process of the invention is generally carried out at a pressure in the range from 1 to 50 bar (a), preferably from 2 to 15 bar (a).

The process of the invention can, in one embodiment, be carried out in the presence of at least one reducing agent. According to the invention, all reducing agents which are able, under the conditions of the process, to reduce the dinitrogen monoxide $N_2O$ which is preferably to be degraded are suitable.

The present invention therefore preferably provides the process of the invention in which at least one reducing agent is additionally used.

Preferred reducing agents are selected from the group consisting of nitrogen compounds, for example $NH_3$, hydrocarbons, for example methane $CH_4$ or propane $C_3H_8$, CO, $SO_2$, $H_2$ and mixtures thereof. Particularly preferred reducing agents are selected from the group consisting of $NH_3$, methane $CH_4$, propane $C_3H_8$, $H_2$ and mixtures thereof.

The present invention therefore preferably provides the process of the invention in which the reducing agent is selected from the group consisting of nitrogen compounds, hydrocarbons, CO, $SO_2$, $H_2$ and mixtures thereof.

Apart from $NH_3$, further suitable nitrogen compounds are, for example, azanes, hydroxyl derivatives of azanes, and also amines, oximes, carbamates, urea or urea derivatives.

An example of an azane is hydrazine.

An example of hydroxyl derivatives of azanes is hydroxylamine.

Examples of amines are primary aliphatic amines such as methylamine.

An example of a carbamate is ammonium carbamate.

Examples of urea derivatives are N,N'-substituted ureas such as N,N'-dimethylurea. Ureas and urea derivatives are preferably used in the form of aqueous solutions.

The way in which the preferably gaseous reducing agent is introduced into the gas stream to be treated can be chosen freely for the purposes of the invention; the reducing agent is preferably introduced upstream (in the flow direction) of the reaction zone. It can also be introduced, for example, into the inlet line upstream of the vessel before the catalyst bed or directly before the bed. The reducing agents can be introduced in the form of gases or in the form of a liquid or aqueous solution which vaporizes in the gas stream to be treated. The introduction of any reducing agent added into the gas to be treated is preferably carried out by means of a suitable device such as an appropriate pressure valve or appropriately configured nozzles.

The amount of any reducing agent added is generally determined so that, based on the nitrogen oxide to be degraded, an approximately equimolar amount of reducing agent is present in the reactor.

The oxygen content of the reaction gas is preferably less than 10% by volume, in particular less than 5% by volume.

The water content of the reaction gas is preferably less than 10% by volume, in particular less than 1% by volume.

In general, preference is given to a relatively low water concentration since higher water contents would make higher operating temperatures necessary. This could, depending on the zeolite type used and the time of operation, exceed the hydrothermal stability limits of the catalyst and therefore has to be matched to the individual case chosen.

The content of nitrogen oxides in the gas stream to be treated can be significantly reduced by the process of the invention. For example, from 10 ppm by volume to 20% by volume, preferably from 200 ppm by volume to 10% by volume, particularly preferably from 500 to 2000 ppm by volume, of the nitrogen oxides, in particular dinitrogen monoxide $N_2O$, present at the beginning are degraded by the process of the invention using the specific above-described zeolite catalyst.

According to the invention, the nitrogen oxides present are catalytically degraded by, preferably, being converted into nitrogen $N_2$ and oxygen $O_2$, in the presence of a reducing agent additionally into the oxidation product of this reducing agent, e.g. in the case of $H_2$ into $H_2O$.

The process of the invention can be used, in particular, in nitric acid production, in adipic acid production, for power station offgases, for gas turbines or for automobile catalysts in the low-temperature range. In these processes, process gases and offgases comprising nitrogen oxide are obtained and can be inexpensively freed of nitrogen oxides by means of the process indicated here.

EXAMPLES

1. Catalyst Preparation

Commercially available zeolites in the H form as powder are used as starting materials for the catalyst preparation. $BEA_{10}$ is the sales product PB/H from Zeochem and MFI$_{17}$ corresponds to PZ 2/25H from the same company. FAU$_{40}$ alias CBV 780, FER$_{10}$ alias CP 914C, BEA$_{140}$ alias CBV 28014 and MFI$_{15}$ alias CBV 3020E can be purchased from Zeochem. BEA$_{140}$ is treated at 450° C. in a hydrogen atmosphere for 4 hours before transition metal and phosphorus and/or sulfur atoms are introduced. This process improves the crystallinity and acidity of the zeolite.

All catalysts are firstly impregnated with iron nitrate solution according to the water uptake of the zeolite. The amount of solution is thus selected so that the solution is completely absorbed by the catalyst and is uniformly distributed in the latter. The amount of iron nitrate is selected so that, after calcination at 550° C. for 4 hours under a nitrogen atmosphere, the indicated amount of iron is comprised in the product. The phosphorus and sulfur contents specified are subsequently obtained by impregnation (according to the water uptake) with appropriately diluted phosphoric or sulfuric acid and renewed calcination under the conditions indicated above. The powders obtained in this way are subsequently compacted without washing or similar process steps and crushed. A fraction having particle sizes from 0.4 to 0.7 mm obtained by sieving is used in the subsequent testing.

2. Testing

The catalyst obtained in this way is installed and tested in a tube reactor. The amount of catalyst corresponds in each case to 0.5 ml. The experiments are carried out at 1.5 bar (a) and a GHSV (gas hourly space velocity) of 8000 standard l$_{gas}$/l$_{cat}$h. Gas entering the reactor and gas leaving the reactor are analyzed to determine the nitrous oxide content by GC analysis (flame ionization detector) in order to be able to calculate the depletion or the conversion.

The mixture of 1000 ppm by volume of N$_2$O, 3% by volume of O$_2$, 0.3% by volume of H$_2$O and the balance to 100% by volume of N$_2$ will hereinafter be referred to as base gas. In this mixture, part of the nitrogen is optionally replaced by further components, as follows: 1000 ppm by volume of NO$_x$ (equilibrium composition of NO and NO$_2$), 2000 ppm by volume of H$_2$, 2000 ppm by volume of NH$_3$ and/or 500 or 2000 ppm by volume of C$_3$H$_3$. These optional additions are in each case indicated in the table for the experiment, with the factors 0.5, 1 and 2 before the addition referring to the amount introduced in 1000 ppm by volume increments.

The results of the individual experiments are shown in tables 1 and 2. The conversion of N$_2$O in the base gas at 300 and 400° C. is reported. In the description of the catalysts used, the subscripts indicate the amount of transition metal or S and/or P present in percent by weight; the amount of zeolite is not indicated since the sum of zeolite, transition metal, S and/or P is in each case 100% by weight. For example, the catalyst Fe$_{2.5}$P$_{0.4}$-BEA$_{140}$ consists of 2.5% by weight of Fe, 0.4% by weight of P and balance to 100% by weight, i.e. 97.1% by weight, of zeolite BEA$_{140}$. "-" means "not determined".

The catalysts denoted by "C" in tables 1 and 2 are comparative examples.

TABLE 1

Conversion of N$_2$O at 300° C. in the base gas

| No. | Catalyst | pure | +NO$_x$ | +NO$_x$ +2•H$_2$ | +NO$_x$ + 2•C$_3$H$_8$ | +2•H$_2$ | +2•C$_3$H$_8$ | +0.5•C$_3$H$_8$ | +2•NH$_3$ | +2•H$_2$ no O$_2$ |
|---|---|---|---|---|---|---|---|---|---|---|
| C1 | Fe$_{2.5}$-BEA$_{10}$ | — | 0% | — | 12% | — | 100% | 84% | 53% | 67% |
| 2 | Fe$_{2.5}$P$_{0.4}$-BEA$_{10}$ | — | 12% | | 27% | 34% | 100% | 100% | 60% | 100% |
| C3 | Fe$_{2.5}$-BEA$_{140}$ | — | — | — | — | — | — | — | — | 96% |
| 4 | Fe$_{2.5}$P$_{0.4}$-BEA$_{140}$ | — | — | — | — | — | — | — | — | 100% |
| C5 | Cu$_{2.5}$-FAU$_{40}$ | — | — | — | — | — | — | — | — | 10% |
| 6 | Cu$_{2.5}$P$_{2.2}$-FAU$_{40}$ | — | — | — | — | — | — | — | — | 17% |
| C7 | Fe$_{2.5}$-FER$_{10}$ | 0% | 5% | 7% | 10% | 7% | 9% | — | 14% | 89% |
| 8 | Fe$_{2.5}$S$_{2.1}$-FER$_{10}$ | 2% | — | 7% | 11% | 18% | 12% | — | 17% | 100% |
| 9 | Fe$_{2.5}$P$_{0.4}$-FER$_{10}$ | 0% | 6% | 7% | 12% | 24% | 14% | — | 32% | 100% |
| 10 | Fe$_{2.5}$P$_{0.7}$-FER$_{10}$ | 5% | 5% | 8% | 12% | 19% | 19% | — | 30% | 100% |
| 11 | Fe$_{2.5}$P$_{1.4}$-FER$_{10}$ | 0% | 4% | 1% | 6% | 14% | 31% | — | 16% | 78% |
| 12 | Fe$_{2.5}$P$_{2.2}$-FER$_{10}$ | — | — | — | — | — | — | — | — | 65% |
| 13 | Fe$_{2.5}$P$_{2.9}$-FER$_{10}$ | 0% | 3% | 0% | 5% | 8% | 18% | — | 12% | 27% |
| 14 | Fe$_{2.5}$P$_{3.6}$-FER$_{10}$ | — | — | — | — | — | — | — | — | 17% |
| C15 | Fe$_{2.5}$-MFI$_{17}$ | 0% | 0% | 0% | 12% | 0% | 91% | — | 14% | n.d. |
| 16 | Fe$_{2.5}$P$_{0.4}$-MFI$_{17}$ | 1% | 2% | 0% | 16% | 8% | 90% | — | 28% | n.d. |
| 17 | Fe$_{2.5}$P$_{0.7}$-MFI$_{17}$ | 2% | 4% | 13% | 15% | 8% | 81% | — | 27% | n.d. |
| 18 | Fe$_{2.5}$P$_{1.1}$-MFI$_{17}$ | 0% | 3% | 0% | 15% | 19% | 88% | — | 26% | n.d. |
| 19 | Fe$_{2.5}$P$_{1.4}$-MFI$_{17}$ | 0% | 4% | 0% | 14% | 7% | 92% | — | 26% | n.d. |

TABLE 2

Conversion of N$_2$O at 400° C. in the base gas

| No. | Catalyst | pure | +NO$_x$ | +NO$_x$ +2•H$_2$ | +NO$_x$ +2•C$_3$H$_8$ | +2•H$_2$ | +2•C$_3$H$_8$ | +2•NH$_3$ | +2•H$_2$ no O$_2$ |
|---|---|---|---|---|---|---|---|---|---|
| C20 | Fe$_{2.5}$-BEA$_{10}$ | — | 78% | — | — | 35% | 100% | — | 100% |
| 21 | Fe$_{2.5}$P$_{0.4}$-BEA$_{10}$ | — | 82% | — | — | 48% | 100% | 69% | 100% |
| C22 | Cu$_{2.5}$-BEA$_{10}$ | — | — | — | — | 12% | — | — | — |
| 23 | Cu$_{2.5}$P$_{0.2}$-BEA$_{10}$ | — | — | — | — | 14% | — | — | — |
| 24 | Cu$_{2.5}$P$_{0.4}$-BEA$_{10}$ | — | — | — | — | 16% | — | — | — |
| 25 | Cu$_{2.5}$P$_{0.8}$-BEA$_{10}$ | — | — | — | — | 12% | — | — | — |
| 26 | Cu$_{2.5}$P$_{1.2}$-BEA$_{10}$ | — | — | — | — | 13% | — | — | — |
| 27 | Cu$_{2.5}$P$_{1.6}$-BEA$_{10}$ | — | — | — | — | 12% | — | — | — |
| C28 | Fe$_{2.5}$-FAU$_{40}$ | — | — | — | — | — | — | — | 77% |
| 29 | Fe$_{2.5}$P$_{2.2}$-FAU$_{40}$ | — | — | — | — | — | — | — | 100% |

TABLE 2-continued

Conversion of N₂O at 400° C. in the base gas

| No. | Catalyst | pure | +NO$_x$ | +NO$_x$ +2•H$_2$ | +NO$_x$ +2•C$_3$H$_8$ | +2•H$_2$ | +2•C$_3$H$_8$ | +2•NH$_3$ | +2•H$_2$ no O$_2$ |
|---|---|---|---|---|---|---|---|---|---|
| C30 | Fe$_{2.5}$-FER$_{10}$ | 2% | 34% | 49% | 62% | 23% | 85% | 22% | 100% |
| 31 | Fe$_{2.5}$P$_{0.4}$-FER$_{10}$ | 2% | 73% | 78% | 89% | 39% | 100% | 34% | 100% |
| 32 | Fe$_{2.5}$P$_{0.7}$-FER$_{10}$ | 9% | 74% | 79% | 80% | 53% | 100% | 55% | 100% |
| 33 | Fe$_{2.5}$P$_{1.4}$-FER$_{10}$ | 2% | 49% | 62% | 50% | 42% | 95% | 24% | 100% |
| 34 | Fe$_{2.5}$P$_{2.2}$-FER$_{10}$ | — | 44% | 59% | — | — | — | — | 100% |
| 35 | Fe$_{2.5}$P$_{2.9}$-FER$_{10}$ | 1% | 28% | 37% | 40% | 38% | 81% | 20% | 76% |
| 36 | Fe$_{2.5}$P$_{3.6}$-FER$_{10}$ | — | 23% | 38% | — | — | — | — | 73% |
| C37 | Fe$_{2.5}$-MFI$_{15}$ | — | — | — | — | — | — | — | 69% |
| 38 | Fe$_{2.5}$P$_{2.2}$-MFI$_{15}$ | — | — | — | — | — | — | — | 74% |
| C39 | Fe$_{2.5}$-MFI$_{17}$ | 1% | 25% | 32% | 68% | 20% | 100% | 50% | — |
| 40 | Fe$_{2.5}$P$_{0.4}$-MFI$_{17}$ | 1% | 34% | 44% | 64% | 29% | 100% | 54% | — |
| 41 | Fe$_{2.5}$P$_{0.7}$-MFI$_{17}$ | 1% | 34% | 29% | 63% | 26% | 100% | 37% | — |
| 42 | Fe$_{2.5}$P$_{1.1}$-MFI$_{17}$ | 2% | 29% | 35% | 74% | 28% | 100% | 47% | — |
| 43 | Fe$_{2.5}$P$_{1.4}$-MFI$_{17}$ | 2% | 33% | 40% | 69% | 19% | 100% | 49% | — |
| C44 | Cu$_{2.5}$-MFI$_{17}$ | — | — | 0% | — | 9% | — | — | — |
| 45 | Cu$_{2.5}$P$_{0.2}$-MFI$_{17}$ | — | — | 8% | — | 14% | — | — | — |
| 46 | Cu$_{2.5}$P$_{0.4}$-MFI$_{17}$ | — | — | 8% | — | 16% | — | — | — |
| 47 | Cu$_{2.5}$P$_{0.8}$-MFI$_{17}$ | — | — | 8% | — | 20% | — | — | — |
| 48 | Cu$_{2.5}$P$_{1.2}$-MFI$_{17}$ | — | — | 9% | — | 18% | — | — | — |
| 49 | Cu$_{2.5}$P$_{1.4}$-MFI$_{17}$ | — | — | 9% | — | — | — | — | — |
| 50 | Cu$_{2.5}$P$_{2.2}$-MFI$_{17}$ | — | — | 9% | — | — | — | — | — |
| 51 | Cu$_{2.5}$P$_{4.1}$-MFI$_{17}$ | — | — | 8% | — | — | — | — | — |

The invention claimed is:

1. A process for reducing the content of nitrogen oxides in a gas comprising contacting said gas with a zeolite catalyst comprising at least one transition metal and sulfur atoms.

2. The process of claim 1, wherein said at least one transition metal is selected from the fourth period and/or groups 8 to 11 of the Periodic Table of the Elements.

3. The process of claim 1, wherein said at least one transition metal is selected from the group consisting of Sc, Ti, V, Cr, Mn, Fe, Co, Ni, Cu, Zn, Ru, Rh, Pd, Ag, Os, Ir, Pt, Au, and mixtures thereof.

4. The process of claim 1, wherein said at least one transition metal is present in said zeolite catalyst in a concentration of from 0.1 to 10.0% by weight, based on the total weight of said zeolite catalyst.

5. The process of claim 1, wherein said sulfur atoms are present in said zeolite catalyst in a concentration of less than 10% by weight, based on the total weight of said zeolite catalyst.

6. The method of claim 5, wherein said sulfur atoms are present in said zeolite catalyst in a concentration of less than 3% by weight, based on the total weight of said zeolite catalyst.

7. The method of claim 5, wherein said sulfur atoms are present in said zeolite catalyst in a concentration in the range of from 0.2 to 2.0% by weight, based on the total weight of said zeolite catalyst.

8. The process of claim 1, wherein the zeolite of said zeolite catalyst is selected from the group consisting of BEA, FAU, FER, MFI, and mixtures thereof.

9. The process of claim 1, wherein said at least one transition metal is Fe, Cu, Co, and/or Ni.

10. The process of claim 1, wherein said method is used in nitric acid production, in adipic acid production, for power station offgases, for gas turbines, or for automobile catalysts in the low-temperature range.

11. The process of claim 1, wherein said process further comprises contacting said gas with at least one reducing agent.

12. The process of claim 11, wherein said at least one reducing agent is selected from the group consisting of nitrogen compounds, hydrocarbons, CO, SO$_2$, H$_2$, and mixtures thereof.

13. The process of claim 1, wherein said process is carried out at a temperature of less than 400° C.

14. The process of claim 1, wherein the GHSV is in the range of from 200 to 200,000 standard lgas/lcat·h.

15. The process of claim 14, wherein the GHSV is in the range of from 5000 to 50 000 standard lgas/lcat·h.

16. The process of claim 14, wherein the GHSV is in the range of from 10 000 to 30 000 standard lgas/lcat·h.

17. A process for producing a zeolite catalyst comprising at least one transition metal and sulfur and/or phosphorus atoms comprising the steps of:
    (a) applying at least one transitional metal or a precursor compound of said at least one transition metal to a zeolite and calcining the zeolite to convert said precursor into said at least one transition metal to obtain a zeolite doped with said at least one transition metal;
    (b) applying the sulfur and/or phosphorus atoms or a precursor compound of said sulfur and/or phosphorus atoms to the doped zeolite from step (a); and
    calcining the zeolite from step (b).

* * * * *